US 11,065,590 B2

(12) United States Patent
Yamaki et al.

(10) Patent No.: US 11,065,590 B2
(45) Date of Patent: Jul. 20, 2021

(54) GAS GENERATION DEVICE AND GAS GENERATION METHOD

(71) Applicant: HITACHI ZOSEN CORPORATION, Osaka (JP)

(72) Inventors: Masahiro Yamaki, Osaka (JP); Hiroyuki Shinomiya, Osaka (JP); Hiroyuki Takano, Osaka (JP); Koichi Izumiya, Osaka (JP)

(73) Assignee: HITACHI ZOSEN CORPORATION, Osaka (JP)

( * ) Notice: Subject to any disclaimer, the term of this patent is extended or adjusted under 35 U.S.C. 154(b) by 0 days.

(21) Appl. No.: 16/758,536

(22) PCT Filed: Sep. 12, 2018

(86) PCT No.: PCT/JP2018/033774
§ 371 (c)(1),
(2) Date: Apr. 23, 2020

(87) PCT Pub. No.: WO2019/082538
PCT Pub. Date: May 2, 2019

(65) Prior Publication Data
US 2020/0254411 A1    Aug. 13, 2020

(30) Foreign Application Priority Data
Oct. 26, 2017   (JP) .............................. JP2017-207139

(51) Int. Cl.
*B01J 7/00*         (2006.01)
*C07C 1/12*         (2006.01)
(Continued)

(52) U.S. Cl.
CPC ...... *B01J 7/00* (2013.01); *C07C 1/12* (2013.01); *F28C 1/00* (2013.01); *F28F 25/02* (2013.01)

(58) Field of Classification Search
CPC .... B01J 2208/00176; B01J 2208/00504; B01J 2208/00628; B01J 2219/00038;
(Continued)

(56) References Cited

U.S. PATENT DOCUMENTS 6,878,174 B1 *   4/2005   Conochie ................. C10L 9/00
                                                            44/620
2010/0015039 A1   1/2010   Doshi et al.
(Continued)

FOREIGN PATENT DOCUMENTS

CN          104312636 A       1/2015
CN          204718480 U      10/2015
(Continued)

OTHER PUBLICATIONS

International Search Report dated Dec. 18, 2018 issued in corresponding international Application No. PCT/JP2018/033774 with English translation.
(Continued)

*Primary Examiner* — Sharon Pregler
(74) *Attorney, Agent, or Firm* — Pillsbury Winthrop Shaw Pittman, LLP

(57) ABSTRACT

The present application is a generation device including a reaction section which generates a product gas and product water in which the product gas is dissolved through an exothermic reaction of gaseous reactants, a cooling tower which cools cooling water that removes heat generated by the exothermic reaction, a cooling water circulation system which circulates the cooling water between the reaction section and the cooling tower, and piping for mixing the product water generated in the reaction section into the cooling water circulation system.

7 Claims, 8 Drawing Sheets

(51) Int. Cl.
*F28C 1/00* (2006.01)
*F28F 25/02* (2006.01)

(58) Field of Classification Search
CPC ......... B01J 8/0278; B01J 8/0453; C07C 9/04;
C07C 2/84; C07C 11/04; C07C 1/12;
C07C 5/327; C07C 1/0425; C07C 1/04;
C07C 1/0485; C07C 4/02; C07C 5/09;
C07C 11/02; C07C 1/042; C07C 1/048;
C07C 319/06; C07C 1/0435; C07C 1/06;
C07C 1/20
See application file for complete search history.

(56) References Cited

U.S. PATENT DOCUMENTS

2015/0376519 A1 12/2015 Noureldin
2018/0086985 A1 3/2018 Von Olshausen et al.

FOREIGN PATENT DOCUMENTS

| | | |
|---|---|---|
| JP | 7-284602 A | 10/1995 |
| JP | 2002-506469 A | 2/2002 |
| JP | 3639861 B1 | 4/2005 |
| JP | 2008-500941 A | 1/2008 |
| JP | 4598994 B2 | 12/2010 |
| JP | 2012-140382 A | 7/2012 |
| JP | 5175072 B2 | 4/2013 |
| JP | 2013-136538 A | 7/2013 |
| JP | 5358909 B2 | 12/2013 |
| WO | 2016/161998 A1 | 10/2016 |

OTHER PUBLICATIONS

Extended European Search Report dated Feb. 3, 2021, issued in corresponding European Patent Application No. 18871167.5 (9 pgs.).

Notification of the First Office Action dated May 13, 2021, issued in corresponding Chinese Patent Application No. 201880068353.1 with English translation (23 pgs.).

* cited by examiner

GAS GENERATION DEVICE AND GAS GENERATION METHOD

CROSS REFERENCE TO RELATED APPLICATIONS

This application is based upon and claims the benefit of priority of the prior Japanese Patent Application No. 2017-207139, filed on Oct. 26, 2017, and International Patent Application No. PCT/JP2018/033774, filed on Sep. 12, 2018, the entire contents of which are incorporated herein by reference.

TECHNICAL FIELD

The present application discloses a gas generation device and a gas generation method.

BACKGROUND ART

For example, PTL 1 to 4 disclose techniques related to devices or methods in which a product gas is generated by chemically reacting gaseous reactants.

CITATION LIST

Patent Literature

[PTL 1] Japanese Patent Laid-Open No. 2012-140382
[PTL 2] Japanese Patent No. 4598994
[PTL 3] Japanese Patent No. 3639861
[PTL 4] Japanese Patent No. 5358909

SUMMARY OF INVENTION

Technical Problem

In a case in which a chemical reaction is accompanied by an exothermic reaction, when temperature control of a part in which the chemical reaction is performed not performed, the temperature of the part in which the chemical reaction is performed fluctuates. Therefore, a reaction conversion rate also changes, which may cause a problem with quality of a generated product gas. In addition, the product gas is not generated stably.

Further, in a case in which product water is generated as a secondary product through the above chemical reaction in addition to a gaseous product and the product water needs to be dehydrated or removed by being condensed, carrying the above reaction out under a pressurized environment and inhibiting a pressure drop due to dehydration to make the reaction conversion rate constant, thereby realizing stable generation of a high quality product gas, can be considered.

However, when the reaction is performed in such a pressurized environment, a possibility of an unreacted reactant and the product being dissolved in the condensed product water increases. In addition, in a case in which the reactant or the product is a combustible gas, it is necessary to consider safety in treating the product water. In order to avoid the above problem, for example, reducing a concentration of the combustible gas in the product water on the basis of a method for removing the combustible gas using a gas-liquid separator or a method in which the product water stored in equipment such as a tank and the combustible gas present inside the equipment such as the tank is volatilized using a blower is conceivable. However, in these methods, a device configuration becomes complicated and operation of the device takes time. Further, separated product water is not effectively used but is discarded.

Therefore, an object of the present application is to provide a technique in which a high-quality product gas is stably generated and separated water is effectively utilized.

Solution to Problem

In the present invention, in order to solve the problem mentioned above, a cooling tower is provided in a generation device and product water is mixed with cooling water cooled in the cooling tower.

In particular, the present invention is a generation device including a reaction section which generates a product gas and product water in which the product gas is dissolved through an exothermic reaction of gaseous reactants, a cooling tower which cools cooling water that removes heat generated by the exothermic reaction, a cooling water circulation system which circulates the cooling water between the reaction section and the cooling tower, and piping for mixing the product water generated in the reaction section into the cooling water circulation system.

With the generation device described above, the heat generated by the exothermic reaction is removed by the cooling water, and a temperature rise in the reaction section is inhibited and the temperature is kept constant. Therefore, the exothermic reaction proceeds stably, and a high-quality product gas is stably generated.

Also, since the product water generated by the exothermic reaction can be reused as a part of the cooling water, effective use of the product water is realized.

Further, since the product water is mixed into the cooling water circulation system, it is cooled in the cooling tower together with the cooling water. In this case, the dissolved gas dissolved in the product water is diffused into the atmosphere in the cooling tower. That is, the dissolved gas is naturally and safely separated from the product water by being mixed into the cooling water circulation system. Therefore, with the generation device described above, the product gas can be stably generated while the dissolved gas dissolved in the product water is safely treated. In addition, since there is no need for dedicated equipment for processing the dissolved gas dissolved in the product water, almost no effort for treating the dissolved gas dissolved in the product water is required.

Also, in a case in which the product water is, for example, product water produced as a by-product in a methanation reaction between carbon dioxide and hydrogen, it does not contain scale components normally contained in tap water, such as calcium carbonate and silica, and accordingly, no scale component is deposited on piping and the like of the generation device. Therefore, an amount of the scale components deposited in the cooling water circulation system can be reduced, thereby reducing the number of maintenance processes related to removal of the scale components.

Also, the cooling tower may have a sprayer which sprays the cooling water flowing from the reaction section into the cooling tower. When such a sprayer is provided in the cooling tower, the dissolved gas dissolved in the product water mixed with the cooling water is diffused into the atmosphere when the cooling water is sprayed and separated from the product water.

Also, the reaction section may have a reaction tower in which the exothermic reaction is performed, a heat medium circulation system which circulates a heat medium that performs heat exchange in the reaction section, and a heat exchanger which exchanges heat between the heat medium of the heat medium circulation system and the cooling water of the cooling water circulation system.

With the generation device described above, it is possible to use a substance other than water as the heat medium which exchanges heat with the reaction section. Further, in a case in which the heat medium absorbs heat from the reaction section, heat is exchanged between the heat medium and the cooling water, and the absorbed heat is removed by the cooling water. Therefore, the heat medium can be circulated to the reaction section and reused to absorb heat from the reaction section, thereby reducing producing costs of the product gas.

Also, the exothermic reaction may be performed at a predetermined temperature higher than a boiling point of water, and the heat medium circulation system may have a heater which heats the heat medium to the predetermined temperature.

Here, the predetermined temperature is a temperature at which the exothermic reaction proceeds. With this generation device, the reaction section is heated to the predetermined temperature due to the heat exchange between the heat medium and the reaction section. Thereafter, since the reaction can proceed in the reaction section, the reaction section is kept at a constant temperature from the start of the reaction, and thus the product gas is generated stably. In addition, when a substance other than water, which is liquid at the predetermined temperature, is used for the heat medium, a pressure in the heat medium system can be inhibited, thereby reducing a load on the generation device.

Also, the exothermic reaction may generate methane and water from hydrogen and carbon dioxide. With this generation device, for example, carbon dioxide which is discharged in large quantities from factories and automobiles and is present in the atmosphere can be used to generate methane, which is an energy resource, and resource recycling is realized.

Also, the present invention can also be understood as an aspect of a method. That is, the present invention may be a generation method including, for example, generating a product gas and product water in which the product gas is dissolved through an exothermic reaction of gaseous reactants in a reaction section; cooling water, which removes heat generated by the exothermic reaction, in a cooling tower; circulating the cooling water between the reaction section and the cooling tower using a cooling water circulation system; and mixing the product water generated in the reaction section into the cooling water circulation system.

Also, the present invention may be a method of operating a generation device, including: heating a reaction section, in which an exothermic reaction of gaseous reactants is performed at a predetermined temperature higher than a boiling point of water, to the predetermined temperature; supplying the reactants to the reaction section heated to the predetermined temperature in the heating step, circulating cooling water between the reaction section, to which the reactants are supplied in the supplying step, and a cooling tower by using a cooling water circulation system that circulates the cooling water between the cooling tower, which cools the cooling water that removes heat generated by the exothermic reaction, and the reaction section; and mixing the product water generated in the reaction section by the exothermic reaction into the cooling water circulation system; stopping supply of reactants to the reaction section; and stopping circulation of cooling water between the reaction section and the cooling tower in the cooling water circulation system after generation of product water in the reaction section, the product water being mixed with the cooling water circulation system, ends.

With the method of operating the generation device described above, the cooling water is circulated to the reaction section which the reactants are supplied and the reaction is being performed. Accordingly, in the heating step, circulation of the cooling water to the reaction section before the reaction is performed is prevented, and wasteful use of the cooling water is inhibited. Since there is no generation of water in which a gas is dissolved before the reaction is performed, mixing of the product water generated in the reaction section into the cooling water circulation system is also unnecessary, and operation of facilities becomes efficient.

Also with the method of operating the generation device described above, circulation of the cooling water is not stopped before the exothermic reaction ends. Therefore, the dissolved gas dissolved in the product water can be safely treated.

Advantageous Effects of the Invention

The above gas generation device and gas generation method can provide a technique in which a high-quality product gas is stably generated and separated water is effectively utilized.

DESCRIPTION OF EMBODIMENTS

Hereinafter, an embodiment of the present invention will be described. The embodiment illustrated below is an example of embodiments of the present invention and does not limit the technical scope of the present invention to the following aspects.

Figure 1:
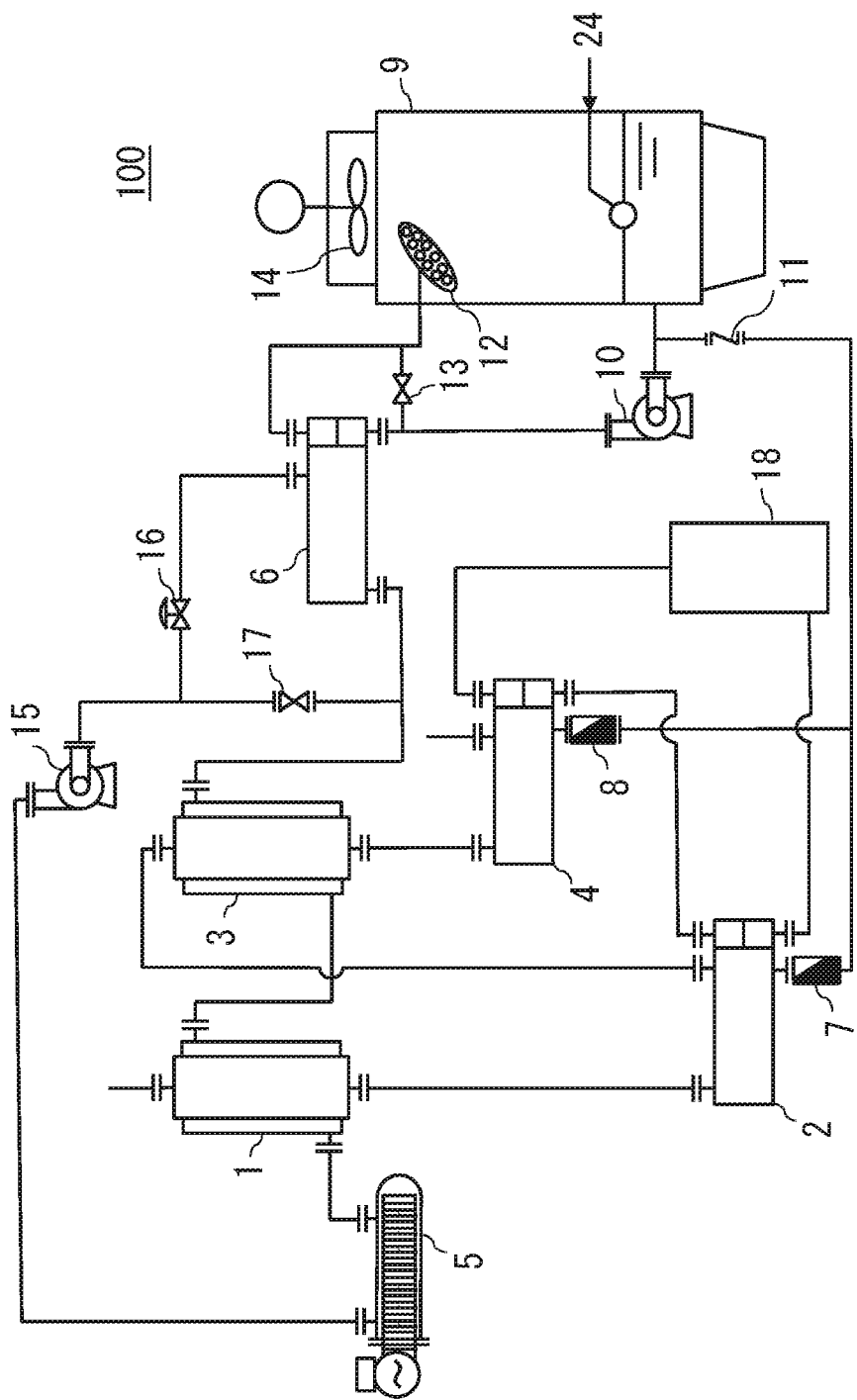
FIG. 1 is a configuration diagram of a generation device according to an embodiment of the present invention.

FIG. 1 is a configuration diagram of a generation device according to an embodiment of the present invention. The generation device 100 shown in FIG. 1 generates methane gas, which is a product gas, and water through an exothermic reaction between gaseous hydrogen and carbon dioxide, for example. Also, the above chemical reaction is also a reversible reaction. The above exothermic reaction is represented by the following chemical reaction formula.

$$4H_2 + CO_2 \leftrightarrows CH_4 + 2H_2O \tag{1}$$

The generation device 100 includes a first stage reaction tower 1 in which gaseous hydrogen and carbon dioxide, which are reactants, are supplied and the aforementioned exothermic reaction is performed. Also, the generation device 100 includes a first stage reaction gas cooling heat exchanger 2 which condenses the water generated in the first stage reaction tower 1 and separates it from the methane gas and unreacted hydrogen and carbon dioxide, and a piping which connects the first stage reaction tower 1 to the first stage reaction gas cooling heat exchanger 2.

Further, the generation device 100 includes a second stage reaction tower 3 which performs the aforementioned exothermic reaction again using the unreacted hydrogen and carbon dioxide after the product water is separated, and generates the methane gas. Also, the generation device 100 includes a piping which connects the first stage reaction gas cooling heat exchanger 2 to the second stage reaction tower 3. The methane gas generated in the first stage reaction tower 1 and the unreacted hydrogen and carbon dioxide are sent to the second stage reaction tower 3 via the first stage reaction gas cooling heat exchanger 2.

Here, the first stage reaction tower 1 and the second stage reaction tower 3 are filled with a catalyst in advance. The catalyst may be any catalyst that promotes the reaction formula (1), and includes, for example, a stabilized zirconia support which has a stabilizing element in a solid solution and has a tetragonal and/or cubic crystal structure, and Ni which is supported on the stabilized zirconia support. Examples of the stabilizing element include a catalyst consisting of at least one transition element selected from the group consisting of Mn, Fe, and Co.

Further, the generation device 100 includes a second stage reaction gas cooling heat exchanger 4 which condenses the water generated in the second stage reaction tower 3 and separates it from the methane gas, and a piping which connects the second stage reaction tower 3 to the second stage reaction gas cooling heat exchanger 4.

The first stage reaction tower 1 and the second stage reaction tower 3 have a jacket structure, and a heat medium that exchanges heat with heat-generating portions in the reaction towers in which the exothermic reaction occurs can flow into and out of jacket portions. Here, for example, a heat medium oil is used for the heat medium. In addition, the generation device 100 includes a heat medium oil heater 5 which heats the heat medium oil that exchanges heat with the first stage reaction tower 1 and the second stage reaction tower 3, and a piping which connects the heat medium oil heater 5 to the jacket portion of the first stage reaction tower 1. Also, the generation device 100 includes a piping which connects the jacket portion of the first stage reaction tower 1 to the jacket portion of the second stage reaction tower 3.

Further, the generation device 100 includes a reaction heat cooling heat exchanger 6 for removing excess heat from the heat medium oil exchanged in the first stage reaction tower 1 and the second stage reaction tower 3, and a piping which connects the jacket portion of the second stage reaction tower 3 to the reaction heat cooling heat exchanger 6.

Further, the first stage reaction gas cooling heat exchanger 2 and the second stage reaction gas cooling heat exchanger 4 are connected to a first stage condensed water drain valve 7 and a second stage condensed water drain valve 8, respectively, which discharge condensed product water. The drain valves may be ones that open and close a valve using buoyancy of a float such as a drain trap or may be ones that electrically detect a water level and open and close a solenoid valve.

Further, the generation device 100 includes a cooling tower 9 which cools the cooling water that exchanges heat with the heat medium oil in the reaction heat cooling heat exchanger 6. In the cooling tower 9, for example, water such as tap water supplied from outside the system is cooled as cooling water. Further, the generation device 100 includes a circulation pump 10 which circulates the cooling water in the cooling tower 9 between the reaction heat cooling heat exchanger 6 and the cooling tower 9. Further, the generation device 100 includes a piping which connects the cooling tower 9 and the circulation pump 10, and a piping through which the product water discharged from the first stage condensed water drain valve 7 and the second stage condensed water drain valve 8 passes. The piping through which the product water discharged from the first stage condensed water drain valve 7 and the second stage condensed water drain valve 8 passes is connected to a middle portion of a suction side pipe of the circulation pump 10. Therefore, the product water is intermittently mixed with the cooling water circulated between the reaction heat cooling heat exchanger 6 and the cooling tower 9. A check valve 11 may be provided in a middle portion of a piping through which the product water discharged from the drain valve passes.

Further, the cooling tower 9 includes a sprayer 12 for spraying the cooling water, which is sent from the cooling tower 9 to the reaction heat cooling heat exchanger 6 by using the circulation pump 10 and returned thereto, into the cooling tower 9. Also, the generation device 100 includes a piping which connects the circulation pump 10 to the reaction heat cooling heat exchanger 6, and a piping which connects the reaction heat cooling heat exchanger 6 and the sprayer 12. In addition, the generation device 100 includes a piping that provides connection between a piping which connects the circulation pump 10 to the reaction heat cooling heat exchanger 6 and a piping which connects the reaction heat cooling heat exchanger 6 to the sprayer 12, and a control valve 13 is provided in a middle portion of the piping. Further, the cooling tower 9 includes a cooling fan 14 for cooling an inside of the cooling tower 9 from above the inside.

Further, the generation device 100 includes a heat medium oil circulation pump 15 which sends the heat medium oil cooled by the reaction heat cooling heat exchanger 6 to the heat medium oil heater 5, a piping which connects the reaction heat cooling heat exchanger 6 to the heat medium oil circulation pump 15, and a piping which connects the heat medium oil circulation pump 15 to the heat medium oil heater 5. In addition, the generation device 100 includes a heat medium oil flow rate control valve 16 in a middle portion of a piping which connects the reaction heat cooling heat exchanger 6 to the heat medium oil circulation pump 15. Also, the generation device 100 includes a piping that provides connection between a piping which connects the second stage reaction tower 3 to the reaction heat cooling heat exchanger 6 and a piping which connects the reaction heat cooling heat exchanger 6 to the heat medium oil circulation pump 15, and a flow rate control valve 17 is provided in a middle portion of the piping.

Further, the generation device 100 includes a chiller 18 which cools the cooling water that exchanges heat with the product water to condense the product water in the first stage reaction gas cooling heat exchanger 2 and the second stage reaction gas cooling heat exchanger 4. In addition, the generation device 100 includes a piping which connects the chiller 18 to the first stage reaction gas cooling heat exchanger 2, a piping which connects the first stage reaction gas cooling heat exchanger 2 to the second stage reaction gas cooling heat exchanger 4, and a piping which connects the second stage reaction gas cooling heat exchanger 4 to the chiller 18.

Figure 2:
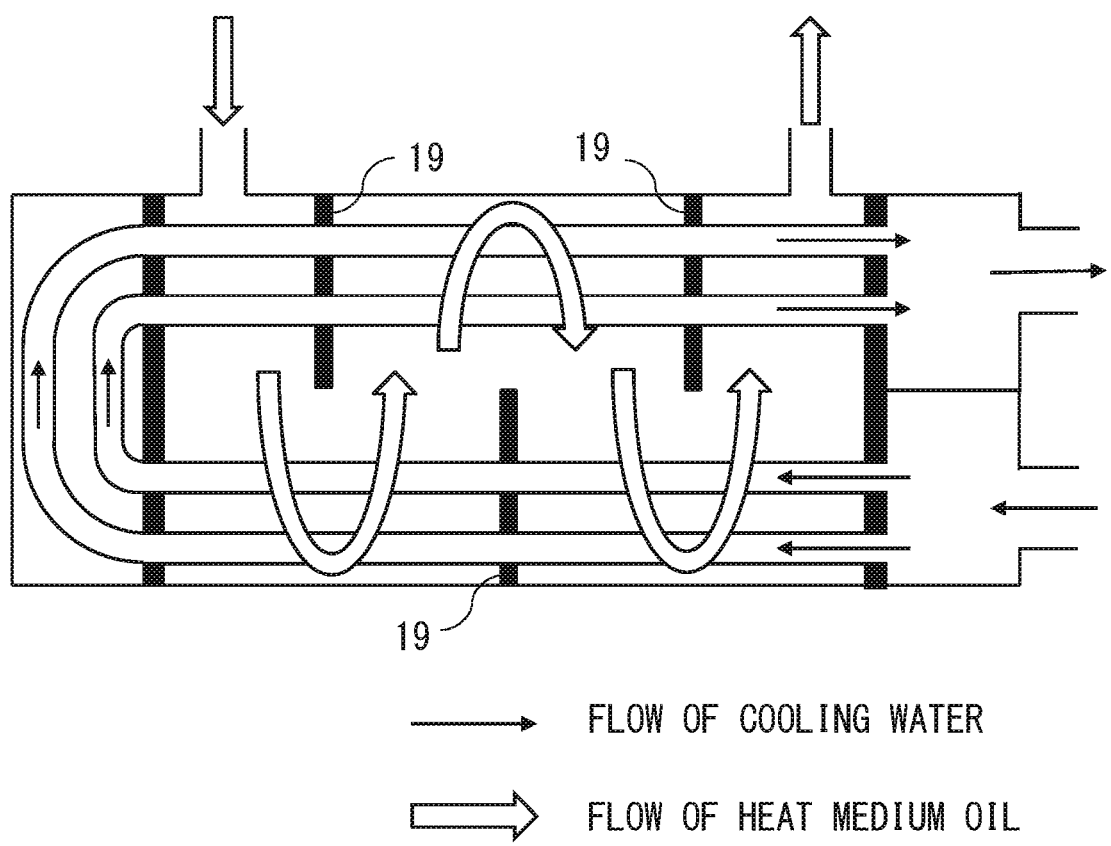
FIG. 2 is an explanatory diagram of a reaction heat cooling heat exchanger.

FIG. 2 is a partially enlarged view of the reaction heat cooling heat exchanger 6. The reaction heat cooling heat exchanger 6 is a so-called shell and tube type heat exchanger. The cooling water circulated from the cooling tower 9 passes through an inside of the tube. On the other hand, inside the shell, the heat medium oil sent from the second stage reaction tower 3 passes therethrough, and exchanges heat with the cooling water. Here, the reaction heat cooling heat exchanger 6 includes a plate 19 for meandering a flow inside the shell. By using the plate 19, the passing heat medium oil is stirred inside the shell and stays for a long time, and thus a heat exchange rate with the cooling water increases. The heat medium oil that has exchanged heat with the cooling water is sent to the heat medium oil circulation pump 15. Also, this shell and tube type heat exchanger may be used for the first stage reaction gas cooling heat exchanger 2 and the second stage reaction gas cooling heat exchanger 4.

<Operation Procedure>

Figure 3:
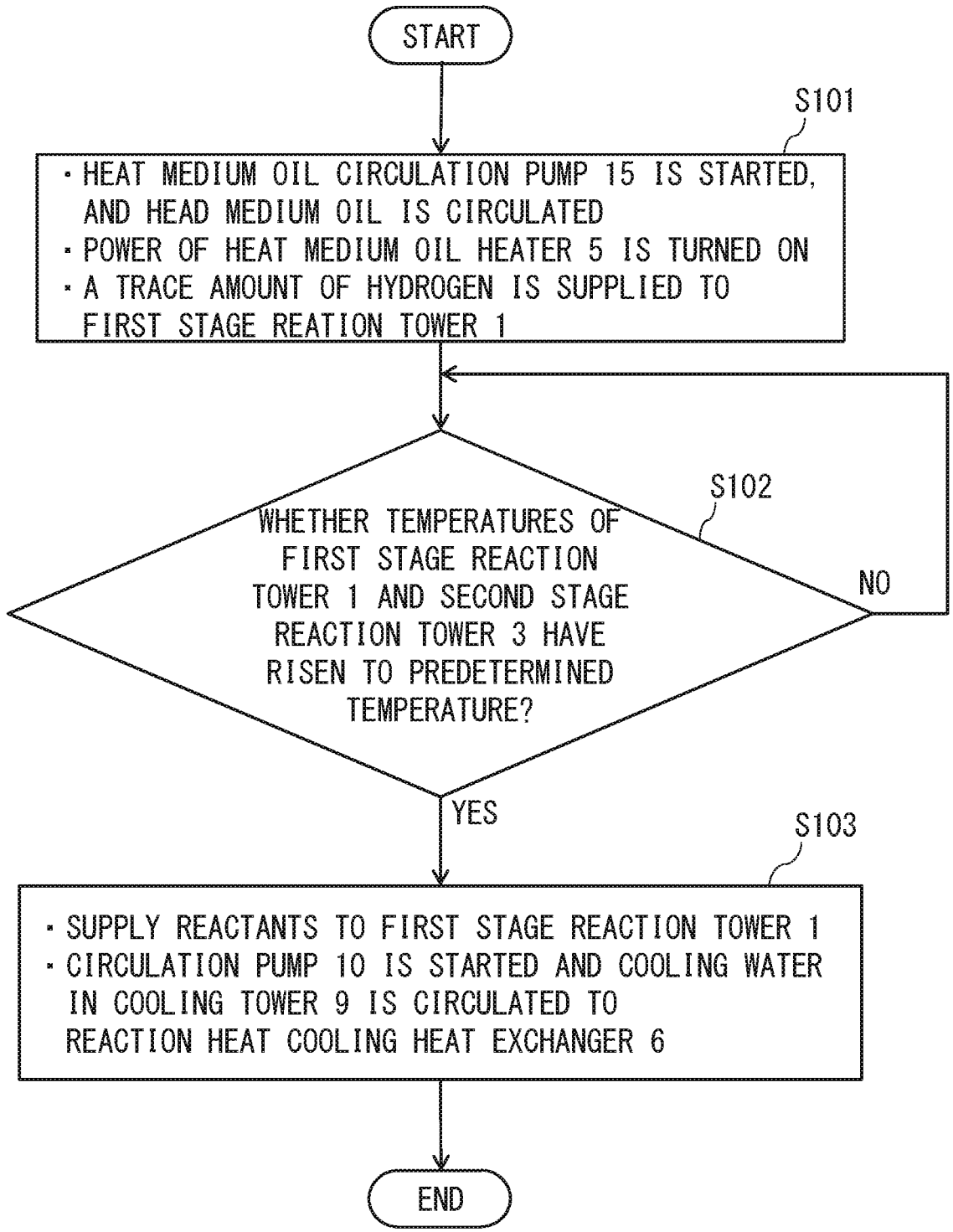
FIG. 3 shows an operation start procedure of the generation device.
Figure 4:
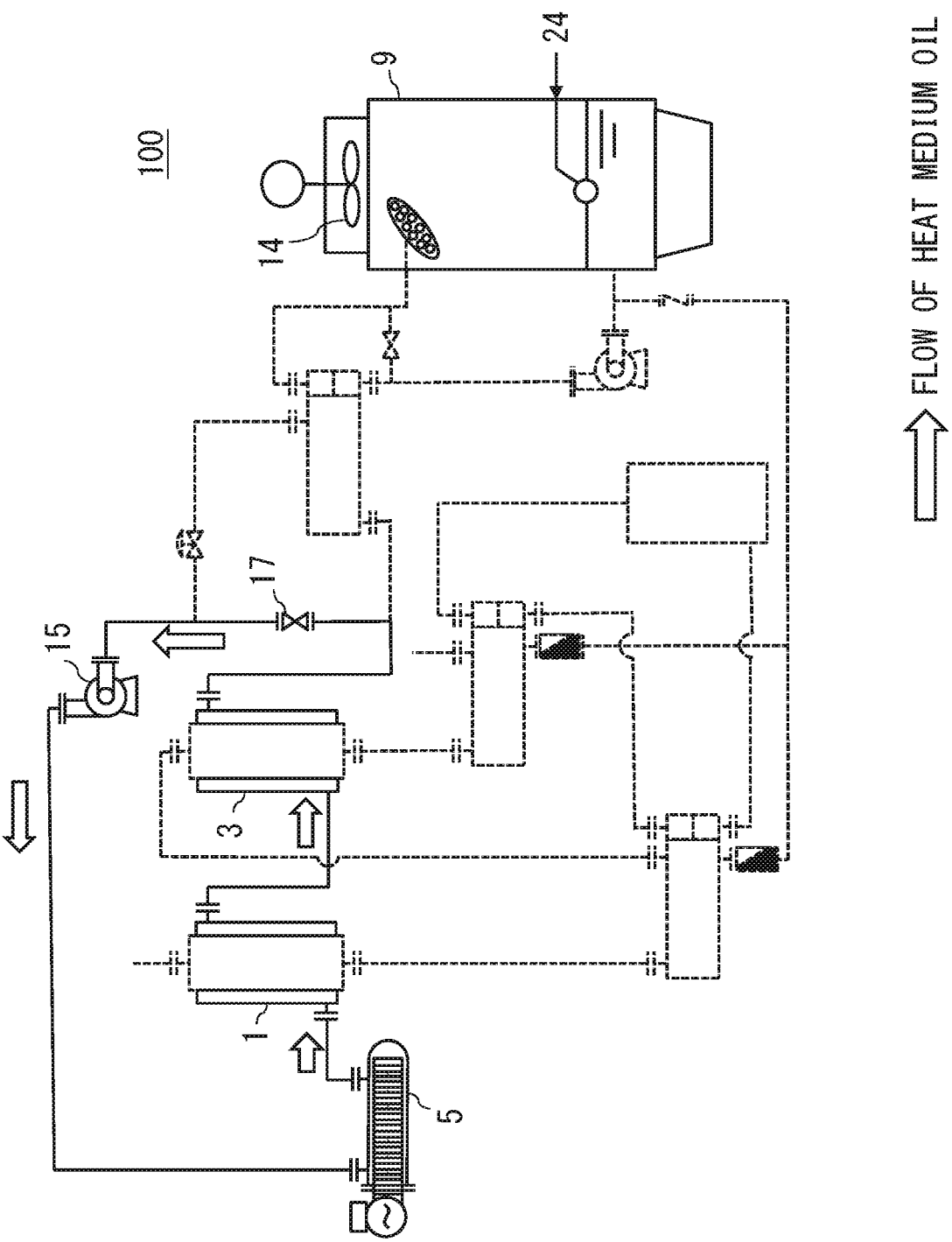
FIG. 4 shows an explanatory diagram of the generation device when an operation starts.
Figure 5:
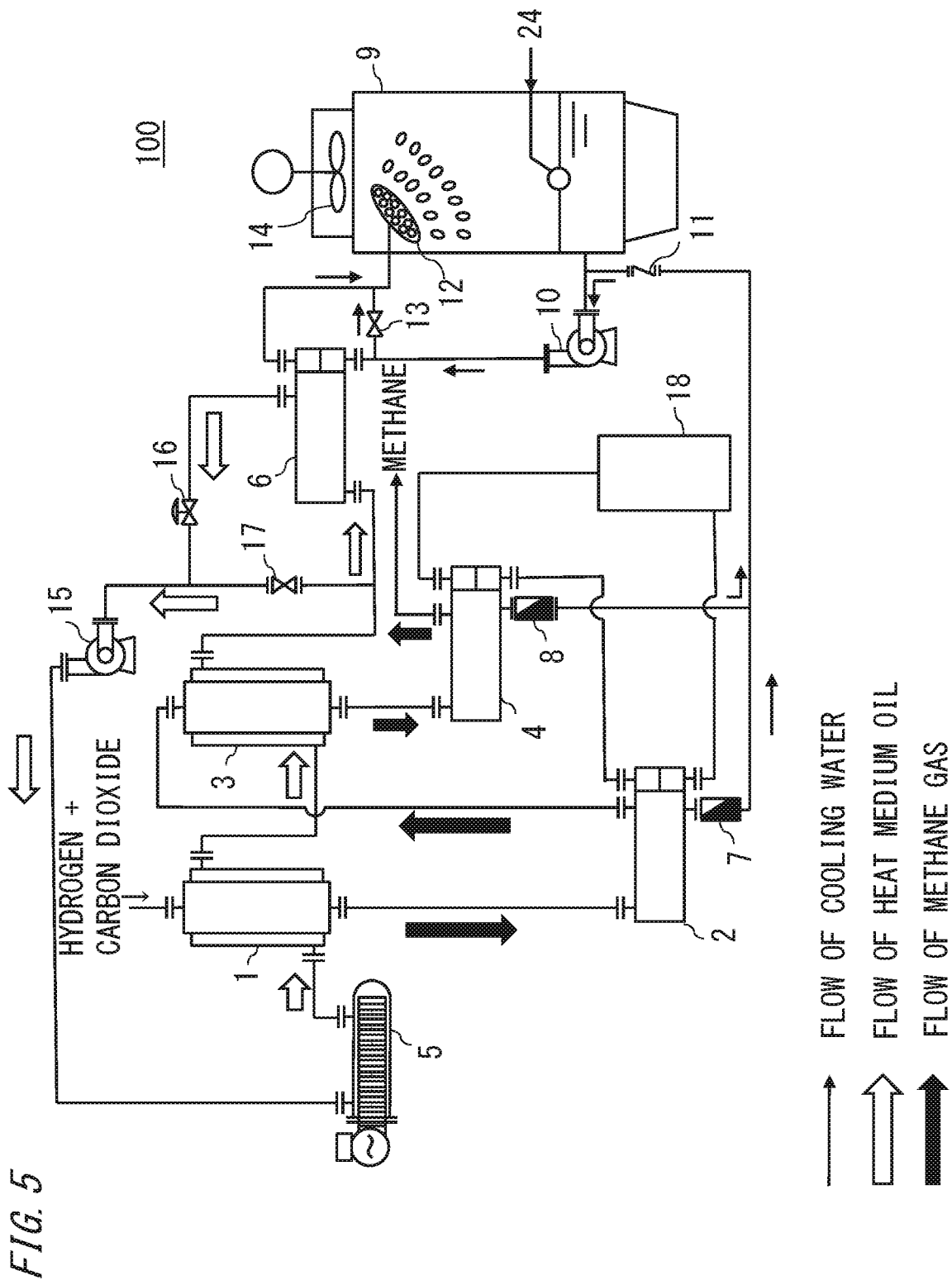
FIG. 5 shows an explanatory diagram of the generation device during operation.

Next, an operation start procedure of the generation device 100 will be described. FIG. 3 shows an operation start procedure of the generation device 100. First, the heat medium oil circulation pump 15 is started, and the power of the heat medium oil heater 5 is turned on. The heat medium oil heated by the heat medium oil heater 5 is sent to the jacket portion of the first stage reaction tower 1. Further, the heat medium oil that has passed through the first stage reaction tower 1 is sent to the jacket portion of the second stage reaction tower 3. Then, the heat medium oil that has passed through the second stage reaction tower 3 is returned to the heat medium oil heater 5, and thereafter, the above operation is repeated. Also, in order to prevent oxidation of active components of the catalyst charged in advance in the first stage reaction tower 1 and the second stage reaction tower 3, for example, a trace amount of hydrogen is supplied to the first stage reaction tower 1 (S101). However, the supplied substance is not limited to hydrogen, and may be a substance having an antioxidant effect, such as nitrogen or carbon dioxide. Also, instead of the above-described supply of the substance for preventing oxidation, a reaction tower having a structure in which oxygen does not enter may be used for the first stage reaction tower 1 and the second stage reaction tower 3. An explanatory diagram of the generation device 100 at this time is shown in FIG. 4. Temperatures of the first stage reaction tower 1 and the second stage reaction tower 3 are observed, and confirmation of whether or not the temperatures of the first stage reaction tower 1 and the second stage reaction tower 3 have risen to a predetermined temperature is performed (S102). Here, the predetermined temperature is a temperature at which the exothermic reaction mentioned above can proceed, for example, about 200° C. In a case in which the temperatures of the first stage reaction tower 1 and the second stage reaction tower 3 have risen to the predetermined temperature, hydrogen and carbon dioxide are supplied to the first stage reaction tower 1. Then, the circulation pump 10 is started, and the cooling water in the cooling tower 9 is circulated to the reaction heat cooling heat exchanger 6 (S103). An explanatory diagram of the generation device 100 in this case is shown in FIG. 5. When the operation start procedure is completed, generation of the product gas and reuse of the product water are performed.

Figure 6:
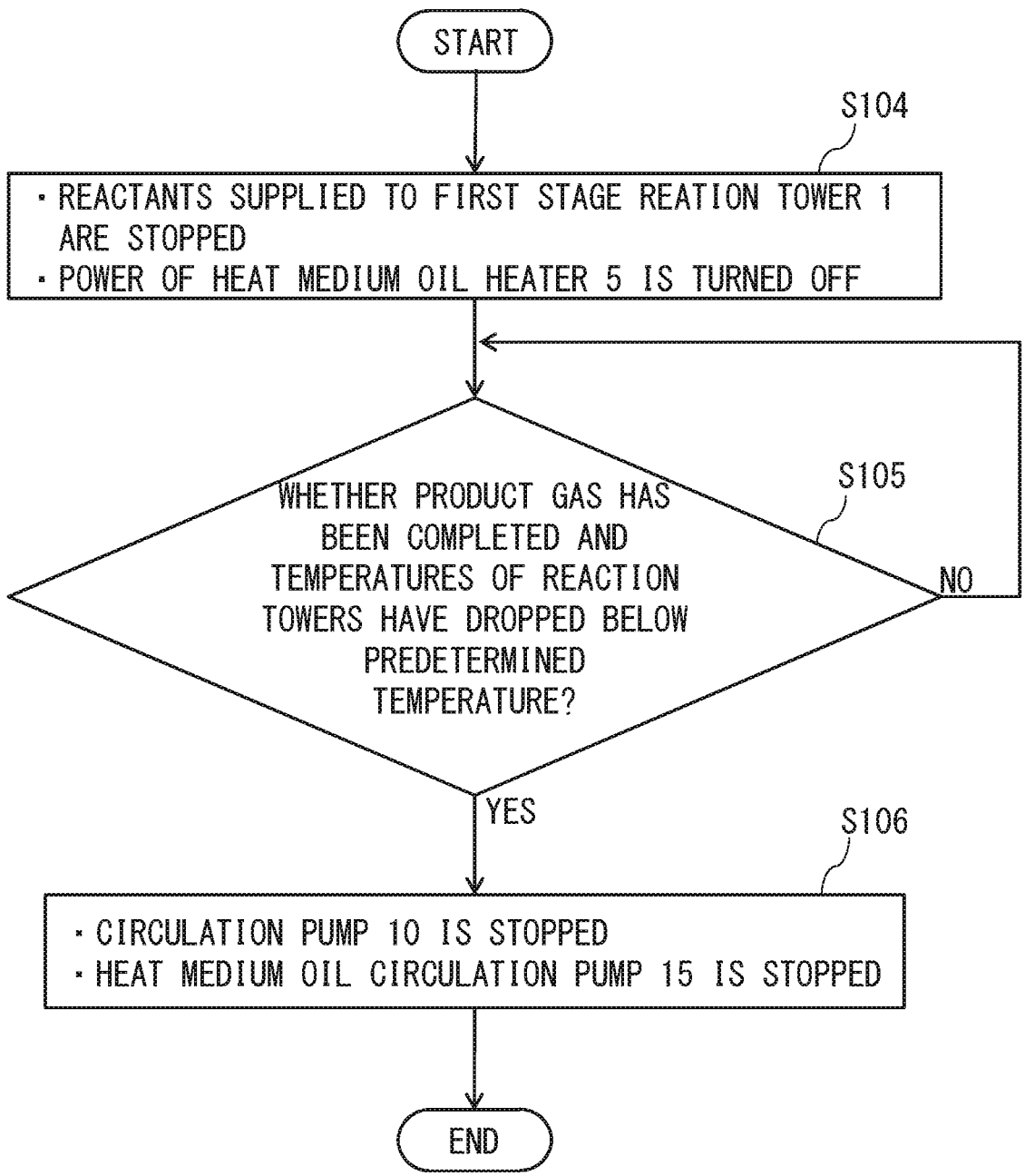
FIG. 6 shows an operation stop procedure of the generation device.
Figure 7:
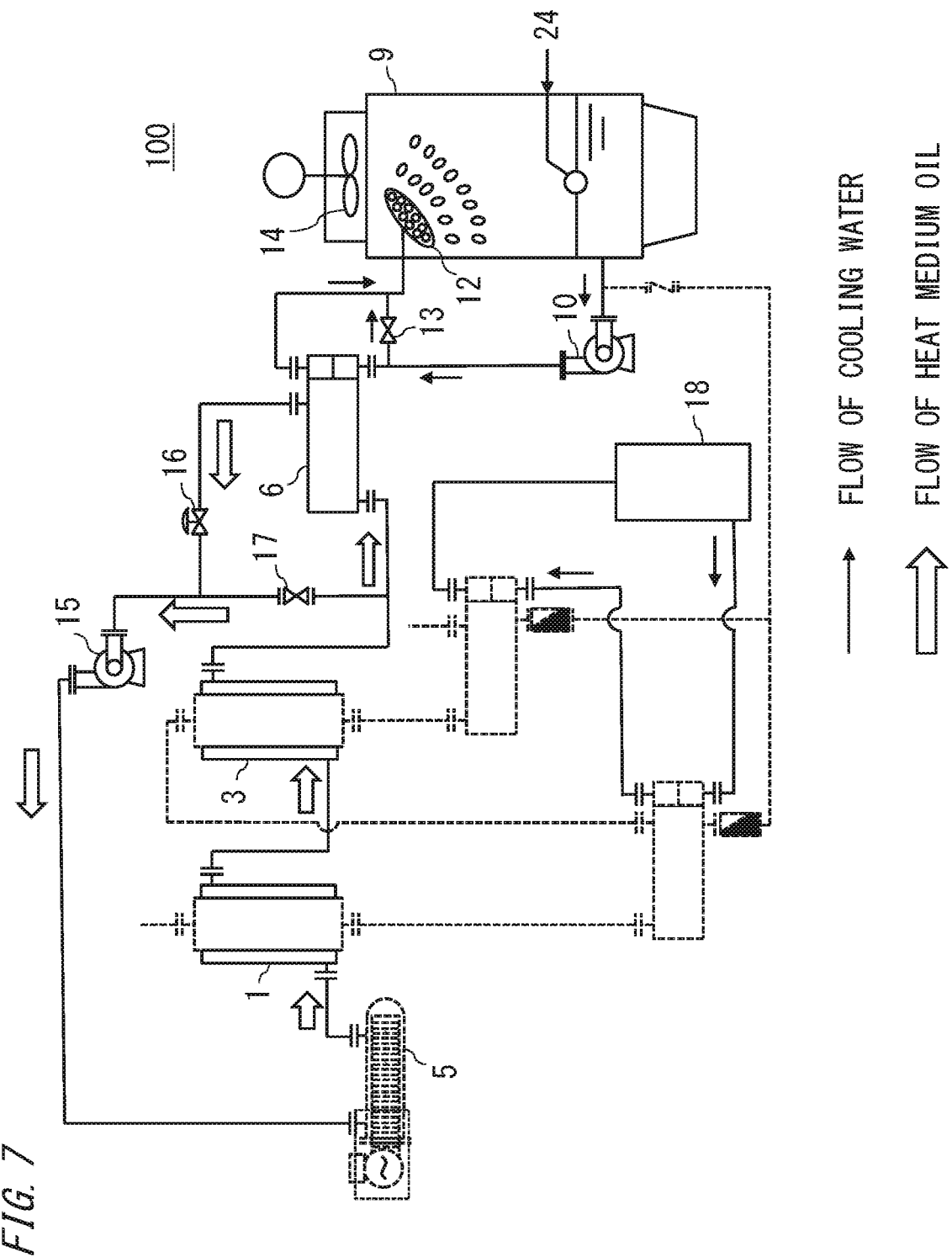
FIG. 7 shows a schematic diagram of the generation device when supply of reactants to a first stage reaction tower is stopped.

Next, an operation stop procedure of the generation device 100 will be described. FIG. 6 shows the operation stop procedure of the generation device 100. Firstly, supply of hydrogen and carbon dioxide to the first stage reaction tower 1 is stopped. Also, the power of the heat medium oil heater 5 is turned off (S104). A schematic diagram of the generation device 100 at this time is shown in FIG. 7. At this time, hydrogen, carbon dioxide, the generated methane, and water vapor remain in the first stage reaction tower 1 and the second stage reaction tower 3, and generation of the product gas is continued by these residues. Then, the temperatures of the first stage reaction tower 1 and the second stage reaction tower 3 are observed and confirmation of whether or not the production of the product gas has been completed is performed. Further, confirmation of whether or not the temperatures of the first stage reaction tower 1 and the second stage reaction tower 3 have dropped below a predetermined temperature (S105) is performed. Here, the predetermined temperature is a lower limit temperature at which the exothermic reaction mentioned above can proceed. Then, in a case in which the temperatures of the first stage reaction tower 1 and the second stage reaction tower 3 have fallen below the predetermined temperature, the circulation pump 10 is stopped, and the circulation of the cooling water is stopped. Also, the heat medium oil circulation pump 15 is stopped (S106).

<Effects>

With the generation device 100 described above, the heat generated by the exothermic reaction in the first stage reaction tower 1 or the second stage reaction tower 3 is removed by the cooling water, and the temperature rise in the first stage reaction tower 1 and the second stage reaction tower 3 is inhibited. Therefore, the exothermic reaction proceeds stably, and high-quality methane is stably generated.

Also, in the generation device 100, the product water which is generated by the exothermic reaction mentioned above and discharged from the first stage condensed water drain valve 7 or the second stage condensed water drain valve 8 passes through the piping connected to the middle portion of the piping which connects the cooling tower 9 to the circulation pump 10 and is mixed with cooling water. Therefore, the product water generated by the exothermic reaction can be reused as a part of the cooling water, and an effective use of the product water is realized.

Further, methane and unreacted hydrogen, which re combustible gases, and carbon dioxide are dissolved in the product water mixed with the cooling water. This product water is cooled in the cooling tower 9 together with the cooling water. During cooling, the methane and unreacted hydrogen and carbon dioxide dissolved in the product water are diffused into the air in the cooling tower. Also, the product water mixed with the cooling water, circulated to the reaction heat cooling heat exchanger 6, and returned to the cooling tower 9 is sprayed from the sprayer 12 into the cooling tower as shown in FIG. 5. During spraying, the methane and unreacted hydrogen and carbon dioxide dissolved in the product water are also diffused into the air in the cooling tower. In other words, combustible gases such as the methane and hydrogen, and carbon dioxide which are dissolved in the product water are separated from the product water spontaneously and not forcibly. Also, the methane, hydrogen, and carbon dioxide which are diffused in the cooling tower are diluted by stirring the atmosphere with the cooling fan 14. Therefore, the methane, which is the product gas, is safely generated. In addition, it does not take time for operation of the device.

Also, since the reaction (1) is a reversible reaction, unreacted reaction gas reacts in the second stage reaction tower 3 after the water produced by the reaction of the reaction gas in the first stage reaction tower 1 is dehydrated and removed. Accordingly, the reaction conversion rate is improved, and concentration of the generated methane is increased.

Further, an amount of heat generated by the exothermic reaction and an amount of water generated by the exothermic reaction follow a reaction rate of the exothermic reaction. That is, when the reaction rate is low, the amount of water generated from the first stage reaction tower 1 and the second stage reaction tower 3 is small, and thus the amount of cooling water circulating to the reaction heat cooling heat exchanger 6 is also small, but the amount of heat generated from the first stage reaction tower 1 and the second stage reaction tower 3 is also small. On the other hand, when the reaction rate is high, the amount of water generated from the first stage reaction tower 1 and the second stage reaction tower 3 increases, and thus the amount of cooling water circulating to the reaction heat cooling heat exchanger 6 also increases, but the amount of heat generated from the first stage reaction tower 1 and the second stage reaction tower 3 is also large. That is, the temperature of the heat medium oil that exchanges heat with the first stage reaction tower 1 and the second stage reaction tower 3 is kept constant irrespective of the reaction rate due to an optimal amount of cooling water, and thus high-quality methane is stably generated.

Also, in a case in which a reaction progress temperature (200° C.) is higher than a boiling point of water as in the present embodiment, when the first stage reaction tower 1 and the second stage reaction tower 3 are directly cooled by the cooling water, the cooling water turns into a gaseous state, and a high pressure is applied inside the jackets of the reaction towers, which imposes a load on the generation device. Therefore, the generation device 100 of the present embodiment removes the reaction heat generated in the first stage reaction tower 1 and the second stage reaction tower 3 by the exothermic reaction described above using the heat medium oil, and cools the heat medium oil containing the reaction heat with the cooling water in the reaction heat cooling heat exchanger 6. When a substance (for example, the heat medium oil) that is in a liquid state at normal pressure at the reaction progress temperature as in the present embodiment is used as the heat transfer medium, a high pressure is not applied to the jacket through which the heat medium passes, and the heat exchange rate with the reaction tower increases since the heat medium oil is a liquid. Therefore, the temperature of the first stage reaction tower 1 and the second stage reaction tower 3 is kept constant without imposing a load on the generation device 100 due to pressure, and generation efficiency of the methane increases. Further, the heat medium oil cooled by the cooling water is sent again to the first stage reaction tower 1 and the second stage reaction tower 3 and used for removing the reaction heat. Thus, production costs of the methane are reduced.

Further, by circulating the heat medium oil, the generation device 100 can not only removes the reaction heat generated from the first stage reaction tower 1 and the second stage reaction tower 3, but can also heat the first stage reaction tower 1 and the second stage reaction tower 3 to a temperature at which the reaction proceeds. Therefore, when the first stage reaction tower 1 is heated to about 200° C. before the reactants are supplied to the first stage reaction tower 1, generation of the methane is performed stably from an initial stage of the reaction.

Also, the cooling water that exchanges heat with the product water to condense the product water in the first stage reaction gas cooling heat exchanger 2 and the second stage reaction gas cooling heat exchanger 4 is supplied from the chiller 18 at a low temperature. Therefore, excellent quality of the generated methane such as dew point and purity is obtained.

In addition, in the method of starting the operation of the generation device 100 as shown in FIG. 3, since the cooling water is circulated in a stage in which the reactants are supplied and the reaction is performed, circulation of the cooling water before the reaction is performed is prevented, and thus wasteful use of the cooling water is inhibited.

Further, with the method of stopping the operation of the generation device 100 as shown in FIG. 6, circulation of the cooling water is not stopped before the exothermic reaction ends.

Also, since the product water generated from the reaction tower does not include scale components usually contained in tap water and the like, for example, calcium carbonate and silica, the scale components do not deposit on the piping or the like of the generation device 100. Therefore, it is unnecessary to perform maintenance of the device such as removing the deposited scale components.

Further, the generation device 100 can use carbon dioxide, for example, which is emitted from factories and automobiles in large quantities and present in the atmosphere, to generate methane that is an energy resource. Therefore, recycling of resources is realized.

<Modified Examples>

Figure 8:
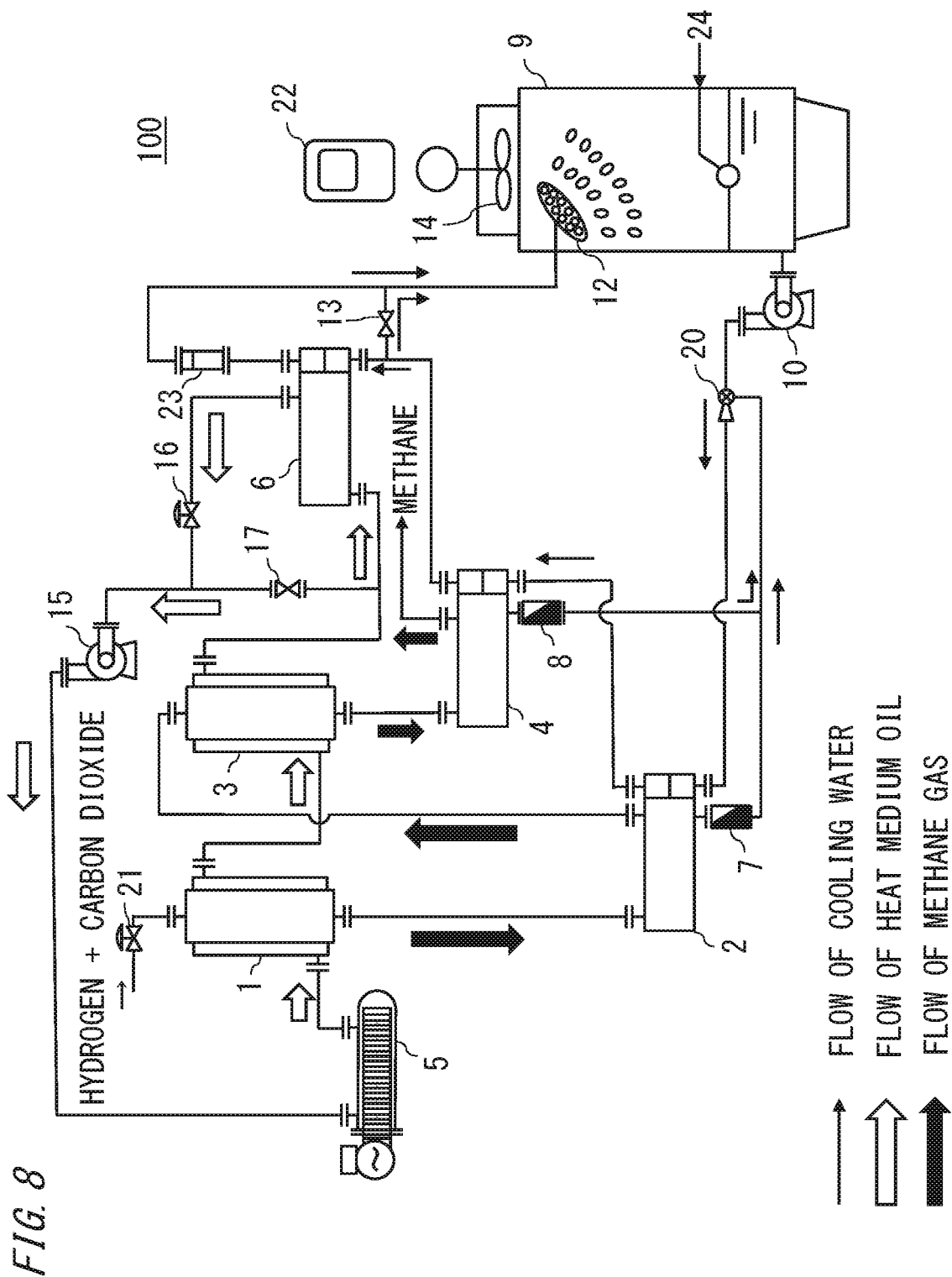
FIG. 8 is a configuration diagram of a modified example of the generation device.

Next, modified examples of the embodiment described above will be described. FIG. 8 is a configuration diagram of a modified example of the generation device 100 of the present embodiment. As shown in FIG. 8, the cooling water that exchanges heat with the product water to condense the product water in the first stage reaction gas cooling heat exchanger 2 and the second stage reaction gas cooling heat exchanger 4 may be supplied not from the chiller 18 but from the cooling tower 9. Also, an ejector 20 may be provided on a discharge side of the circulation pump 10, and the product water discharged from the first stage condensed water drain valve 7 and the second stage condensed water drain valve 8 may be mixed with cooling water.

In addition, in the generation device 100, when the first stage condensed water drain valve 7 and the second stage condensed water drain valve 8 cause a failure such as sticking in the cooling water, a large amount of methane gas, hydrogen, and carbon dioxide are mixed into the cooling water. In such a case, a shut-off valve 21 may be provided in front of the first stage reaction tower 1 in order not to supply hydrogen and carbon dioxide to the first stage reaction tower 1. Further, a gas detector 22 which can detect hydrogen and methane gas may be provided at an upper portion of the cooling tower 9, and the shut-off valve 21 may be configured to be interlocked when an abnormality is detected by the gas detector 22. Also, flow meter 23 may be provided instead of the gas detector 22. The flow meter 23 may detect a decrease in flow rate resulting from an outflow of gas into the cooling water line, for example, using an area flow meter.

With the generation device 100 described above, when the drain valves cause a failure and a large amount of methane gas, hydrogen, and carbon dioxide is mixed in the cooling water, the operation can be stopped quickly.

Also, although the two reaction towers are provided in the present embodiment, the number of reaction towers may be one, three, four, or any number. Also, although the heat medium oil is used as the heat medium that exchanges heat with the reaction towers in the present embodiment, a substance suitable for use conditions, such as a molten salt or high-pressure water, may be used for the heat medium in consideration of the use conditions such as use temperatures and use facilities. Also, some of the heat medium oil that has exchanged heat with the first stage reaction tower 1 may be sent to the reaction heat cooling heat exchanger 6 without passing through the second stage reaction tower 3. In addition, when the exothermic reaction performed in the reaction tower proceeds at 100° C. or lower, normal pressure water in a liquid state may be used as a heat medium that exchanges heat with the reaction tower and removes reaction heat generated by the exothermic reaction. Also, the generation device 100 may also be used when the reaction performed in the reaction tower is an irreversible reaction. Further, the generation device 100 may also be used for the case in which the reaction performed in the reaction tower is an endothermic reaction, and a heat medium that exchanges heat with the reaction tower during the endothermic reaction may supply heat to the reaction tower to keep a temperature of the reaction tower constant.

REFERENCE SIGNS LIST

1 First stage reaction tower
2 First stage reaction gas cooling heat exchanger
3 Second stage reaction tower
4 Second stage reaction gas cooling heat exchanger
5 Heat medium oil heater
6 Reaction heat cooling heat exchanger
7 First stage condensed water drain valve
8 Second stage condensed water drain valve
9 Cooling tower
10 Circulation pump
11 Check valve
12 Sprayer
13 Control valve
14 Cooling fan
15 Heat medium oil circulation pump
16 Heat medium oil flow rate control valve
17 Flow rate control valve
18 Chiller
19 Plate
20 Ejector
21 Shut-off valve
22 Gas detector
23 Flow meter
24 Tap water
100 generation device

The invention claimed is:

1. A generation device comprising:
a reaction section which generates, through an exothermic reaction of gaseous reactants, a product gas and product water in which the product gas is dissolved;
a cooling tower which cools cooling water that removes heat generated by the exothermic reaction;
a cooling water circulation system which circulates the cooling water between the reaction section and the cooling tower; and
piping for mixing the product water generated in the reaction section into the cooling water circulation system.

2. The generation device according to claim 1, wherein the cooling tower includes a sprayer which sprays the cooling water flowing from the reaction section into the cooling tower.

3. The generation device according to claim 1, wherein the reaction section includes:
a reaction tower in which the exothermic reaction is performed;
a heat medium circulation system which circulates a heat medium that performs heat exchange in the reaction tower; and
a heat exchanger which exchanges heat between the heat medium of the heat medium circulation system and the cooling water of the cooling water circulation system.

4. The generation device according to claim 3, wherein the exothermic reaction is performed at a predetermined temperature higher than a boiling point of water, and the heat medium circulation system includes a heater which heats the heat medium to the predetermined temperature.

5. The generation device according to claim 1, wherein the exothermic reaction generates methane and water from hydrogen and carbon dioxide.

6. A generation method comprising:
generating a product gas and product water in which the product gas is dissolved through an exothermic reaction of gaseous reactants in a reaction section;
cooling water for removing heat generated by the exothermic reaction, in a cooling tower;
circulating the cooling water between the reaction section and the cooling tower using a cooling water circulation system; and
mixing the product water generated in the reaction section into the cooling water circulation system.

7. A method of operating a generation device comprising:
heating, to the predetermined temperature, a reaction section in which an exothermic reaction of gaseous reactants is performed at a predetermined temperature higher than a boiling point of water;
supplying the reactants to the reaction section heated to the predetermined temperature in the heating step;
circulating cooling water between the reaction section to which the reactants are supplied in the supplying step and a cooling tower by using a cooling water circulation system that circulates the cooling water between the cooling tower which cools the cooling water that removes heat generated by the exothermic reaction, and the reaction section;
mixing the product water generated in the reaction section by the exothermic reaction into the cooling water circulation system;
stopping supply of reactants to the reaction section; and
stopping circulation of cooling water between the reaction section and the cooling tower in the cooling water circulation system after generation of product water in the reaction section, the product water being mixed with the cooling water circulation system, ends.

* * * * *